(12) United States Patent
Ashkenazi

(10) Patent No.: US 9,404,725 B2
(45) Date of Patent: Aug. 2, 2016

(54) SYSTEM AND METHOD FOR MEASURING GEOMETRY OF NON-CIRCULAR TWISTED STRAND DURING STRANDING PROCESS

(71) Applicant: Ronen Ashkenazi, Gedera (IL)

(72) Inventor: Ronen Ashkenazi, Gedera (IL)

( * ) Notice: Subject to any disclaimer, the term of this patent is extended or adjusted under 35 U.S.C. 154(b) by 27 days.

(21) Appl. No.: 14/302,426

(22) Filed: Jun. 12, 2014

(65) Prior Publication Data

US 2014/0366392 A1    Dec. 18, 2014

(51) Int. Cl.
  *G01B 5/20*    (2006.01)
  *B65H 43/04*    (2006.01)
  *G01B 5/04*    (2006.01)
  *G01B 5/10*    (2006.01)
  *G01D 5/04*    (2006.01)
  *G01N 21/00*    (2006.01)
  *D07B 7/02*    (2006.01)

(52) U.S. Cl.
  CPC ............... *G01B 5/201* (2013.01); *B65H 43/04* (2013.01); *D07B 7/022* (2013.01); *G01B 5/043* (2013.01); *G01B 5/10* (2013.01); *G01B 5/20* (2013.01); *G01D 5/04* (2013.01); *G01N 21/00* (2013.01); *D07B 2301/55* (2013.01)

(58) Field of Classification Search
  CPC ........... G01B 5/201; G01B 5/043; G01B 5/10
  USPC .................. 33/1 PT, 555.1, 734, 735, 501.02, 33/501.03
  See application file for complete search history.

(56) References Cited

U.S. PATENT DOCUMENTS

| 2,876,549 | A | * | 3/1959 | Adamson | G01B 5/043 33/734 |
| 3,091,038 | A | * | 5/1963 | Brand | E21B 47/04 33/734 |
| 4,570,348 | A | * | 2/1986 | Amsler | G01B 7/046 33/734 |
| 4,852,263 | A | * | 8/1989 | Kerr | E21B 47/04 324/206 |
| 5,065,527 | A | * | 11/1991 | Shaw | G01B 5/043 33/734 |
| 5,245,760 | A | * | 9/1993 | Smart | G01B 5/04 33/735 |
| 2005/0217126 | A1 | * | 10/2005 | Inoue | G01D 5/04 33/1 PT |
| 2013/0248638 | A1 | * | 9/2013 | Luo | E01D 21/00 242/470 |
| 2015/0033566 | A1 | * | 2/2015 | Chen | G01D 5/04 33/1 PT |

* cited by examiner

*Primary Examiner* — G. Bradley Bennett
(74) *Attorney, Agent, or Firm* — Daniel J. Swirsky; AlphaPatent Associates Ltd.

(57) ABSTRACT

A system (12) for measuring geometry of a non-circular twisted strand (10) during a stranding process, the system comprising: a pulley (14), for being rotated by linear displacement of the strand (10) induced by the stranding process; a first encoder (16), for measuring the rotation of the pulley (14), thereby measuring the linear displacement of the strand (10); at least one embracing element (36), for embracing a vertex (38) or another zone (48) of the strand (10), for being rotated perpendicular (60) to the longitudinal position (58) of the strand (10), the embracing obtained by the non-circular character of the strand (10) rather than by friction, thereby allowing sliding the at least one embracing element (36) therealong; and a second encoder (20), for measuring the rotation of the at least one embracing element (36), thereby measuring the twist character of the strand (10).

20 Claims, 4 Drawing Sheets

SYSTEM AND METHOD FOR MEASURING GEOMETRY OF NON-CIRCULAR TWISTED STRAND DURING STRANDING PROCESS

TECHNICAL FIELD

The present invention relates to the field of strand processing. More particularly, the invention relates to a method and apparatus for measuring the geometry of a non-circular twisted strand during the stranding process.

BACKGROUND ART

Ropes and cables are constructed of helical strands. The strand shape/cross-section/profile can be circular or non-circular. Typical non-circular strands include vertexes.

The term "stranding process" refers herein to the manufacturing process of the strand.

During the stranding process, geometrical parameters of the strand must be controlled and measured. The quality of the strand and of the rope is obtained accordingly.

Geometrical parameters and features of the strand include: roundness and uniformity of the strand surface, critical dimensions of the strand shape, lay length of the twisted non-circular strand construction, any geometrical parameter that may impact the position of the strand when it is closed into the rope configuration, the final principal dimensions of the rope and the outer surface of the rope.

Any anomaly/defect/fault generated during the stranding process of the strand may generate a critical anomaly anomaly/defect/fault at the rope level. The presence of anomaly/defect/fault at the rope level can cause the discarding of the rope during the rope closing process. Moreover, if the anomaly/defect/fault is not detected during the strand manufacturing process or at the rope closing process, the rope may be supplied to the customer defected.

The anomaly/defect/fault can generate degradation/damage/interference to the rope performance and mechanical behavior. This can generate damage to the application, impacting the safety level, impacting the installation's performance and causing a considerable reduction in service life.

There is a need for an online/real time procedure and system for the detection of geometrical anomalies/defects/faults, during the stranding process of non-circular and circular strands.

This may avoid disqualification of the rope at the manufacturer or at the customer or end user side. The online/real time procedure and system for the detection, providing the quality assurance (QA), may eliminate manufacturing expenses.

Thus, it is an object of the present invention to provide a method and system for measuring the geometry of the non-circular strand during the manufacturing thereof.

It is another object of the present invention to detect defects during the stranding process.

It is an object of the present invention to provide a solution to the above-mentioned and other problems of the prior art.

Other objects and advantages of the invention will become apparent as the description proceeds.

SUMMARY OF THE INVENTION

In one aspect, the present invention is directed to a system (12) for measuring geometry of a non-circular twisted strand (10) during a stranding process, the system comprising:
- a pulley (14), for being rotated by linear displacement of the strand (10) induced by the stranding process;
- a first encoder (16), for measuring the rotation of the pulley (14) in relation to a stationary base (50), thereby measuring the linear displacement of the strand (10);
- at least one embracing element (36), for embracing a vertex (38) or another zone (48) of the strand (10), for being rotated perpendicular (60) to the longitudinal position (58) of the strand (10) upon the linear displacement thereof, due to the twist thereof, the embracing obtained by the non-circular character of the strand (10) rather than by friction, thereby allowing sliding the at least one embracing element (36) therealong; and
- a second encoder (20), for measuring the rotation of the at least one embracing element (36) perpendicular (60) to the longitudinal position (58) of the strand (10) in relation to the stationary base (50), thereby concurrent measurement of the linear displacement of the strand (10) and of the rotation of the at least one embracing element (36) provides a measurement of the twist character of the strand (10).

The number of the at least one embracing elements (36) may comprise the number of vertexes (38) of the strand (10) designed to be produced by the stranding process,
thereby each of the at least one embracing element (36) embraces one of the vertexes (38).

The at least one embracing element (36) is shaped substantially complementary to a shape of the vertexes (38) of the strand (10) designed to be produced by the stranding process.

The at least one embracing element (36) may comprise at least one pulley, for freely rotating along and upon the strand (10).

The at least one embracing element (36) may comprise a springy element (28), for pressing the at least one embracing element (36) on the strand (10).

The at least one embracing element (36) may comprise a plurality of embracing elements (36) surrounding the strand (10),
thereby avoiding bending the strand (10).

The system (12) may further comprise:
at least one slideable surface sensor (40), for traveling together with the at least one embracing element (36), and for sliding along and attached to a zone (48) of the strand (10), for detecting deviations of a surface of the zone (48) from a pre-determined design of the stranding process.

The at least one slideable surface sensor (40) may comprise a position measurement sensor, for detecting the deviations.

The at least one slideable surface sensor (40) may comprise a brush element (62) for conducting electric signals from the at least one slideable surface sensor (40) to a stationary location (24).

The system (12) may further comprise:
a disk (32), connected to the at least one embracing element (36), for being rotated thereby perpendicular (60) to the longitudinal position (58) of the strand (10).

The system (12) may further comprise:
at least one springy element (28), for pressing the at least one embracing element (36) from the disk (32) onto the strand (10).

The system (12) may further comprise:
a wheel (18) disposed at a margin of the disk (32), for being rotated by the disk (32) via a gear system (46), wherein the wheel (18) is connected to the second encoder (20), thereby the second encoder (20) is disposed away from a center of the disk (32).

The system (12) may further comprise:
a controller (24), for determining samples for the measurements, thereby the measurements do not accumulate errors.

The samples may comprise length segments, and/or angular segments.

In another aspect, the present invention is directed to a method for measuring geometry of a non-circular twisted strand (10) during a stranding process, the method comprising the steps of:

rotating a pulley (14) by linear displacement of the strand (10) induced by the stranding process;

measuring, by a first encoder (16), the rotation of the pulley (14), thereby measuring the linear displacement of the strand (10);

embracing, by at least one embracing element (36), a vertex (38) or another zone (48) of the strand (10), for rotating the at least one embracing element (36) perpendicular (60) to the longitudinal position (58) of the strand (10) upon the linear displacement thereof, due to the twist thereof; and measuring, by a second encoder (20), the rotation of the at least one embracing element (36) perpendicular (60) to the longitudinal position (58) of the strand (10), thereby concurrent measurement of the linear displacement of the strand (10) and of the rotation of the at least one embracing element (36), provides a measurement of the twist character of the strand (10).

The embracing of the vertex (38) or another zone (48) of the strand (10) may comprise free linear displacement of the strand (10) in relation to the at least one embracing element (36).

The method may further comprise the steps of:

rotating at least one slideable surface sensor (40) together with the at least two embracing elements (36); and detecting by the at least one slideable surface sensor (40) deviations of a surface of the strand (10) from a pre-determined design of the stranding process, The method may further comprise the steps of:

upon exceeding a pre-determined threshold of measurement, halting the standing process.

The measurements may be conducted upon pre-determined samples of the strand (10), thereby the measurements do not accumulate errors.

The reference numbers have been used to point out elements in the embodiments described and illustrated herein, in order to facilitate the understanding of the invention. They are meant to be merely illustrative, and not limiting. Also, the foregoing embodiments of the invention have been described and illustrated in conjunction with systems and methods thereof, which are meant to be merely illustrative, and not limiting.

BRIEF DESCRIPTION OF DRAWINGS

Preferred embodiments, features, aspects and advantages of the present invention are described herein in conjunction with the following drawings.

It should be understood that the drawings are not necessarily drawn to scale.

DESCRIPTION OF EMBODIMENTS

The present invention will be understood from the following detailed description of preferred embodiments ("best mode"), which are meant to be descriptive and not limiting. For the sake of brevity, some well-known features, methods, systems, procedures, components, circuits, and so on, are not described in detail.

Figure 1:
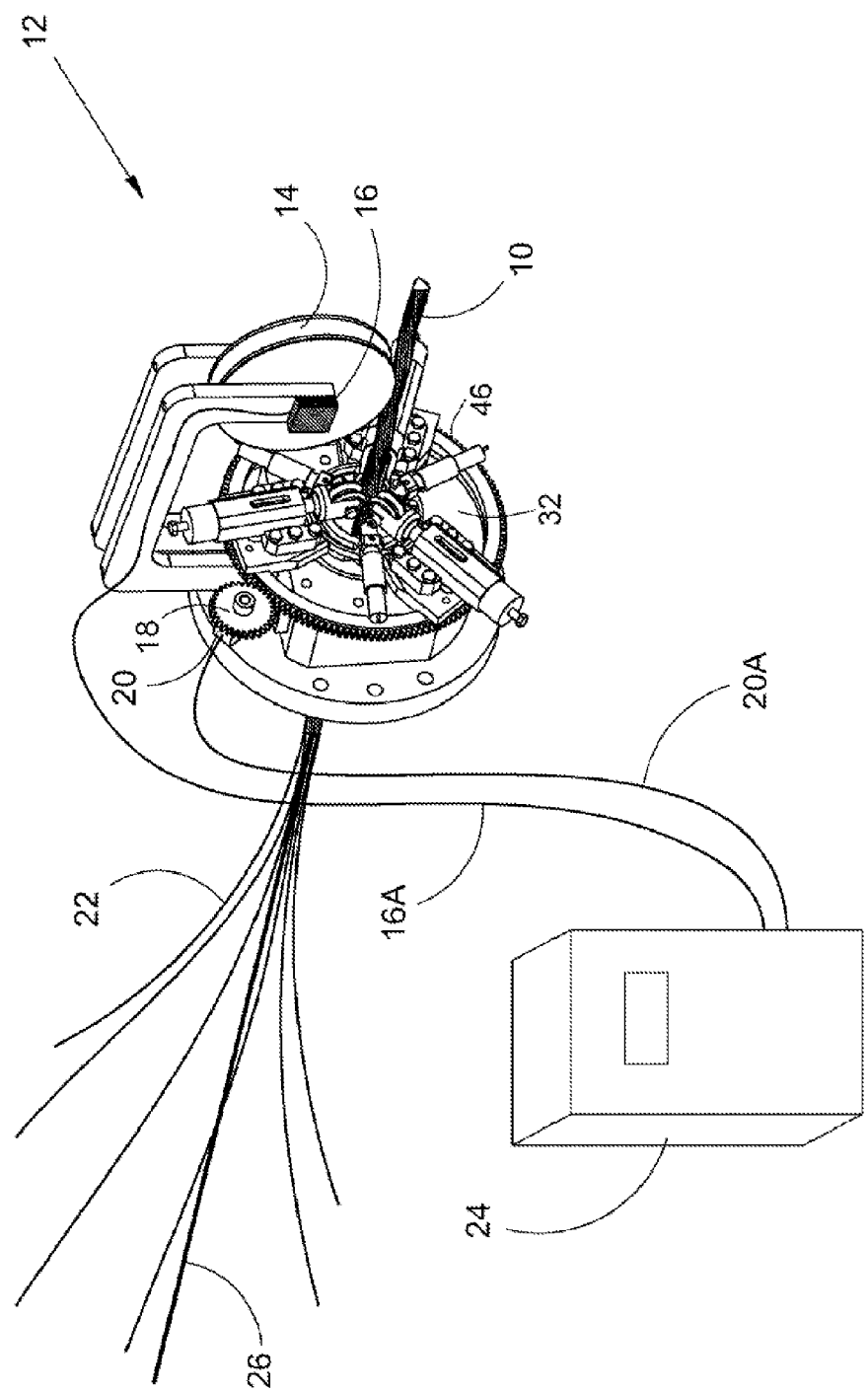
FIG. 1 is a perspective view of a strand scanner, according to one embodiment of the present invention.

FIG. 1 is a perspective view of a strand scanner, according to one embodiment of the present invention.

A strand 10, to be measured and examined by a strand scanner 12, being a system for scanning strand 10, according to one embodiment of the present invention, includes a plurality of wires 22 braided around a core 26. The longitudinal core 26 is of a non-circular shape (not shown), e.g., triangular or oval shape, and is also twisted. Thus, strand 10 including wires 22, surrounding longitudinal core 26, as well is non-circularly shaped and also is twisted as shown in the figure.

FIG. 1 shows a typical constitution of a non-circular strand 10. The manufacturing of strand 10 is performed by a stranding machine, which is not shown in the figures.

Strand scanner 12 according to the present invention may be disposed either at the front end of the machine (not shown) or at any independent disposition for measuring and examining the produced strand 10.

Strand scanner 12, according to one embodiment of the present invention, provides an applicable solution for the need to measure critical geometrical parameters/features of the non-circular strand 10 profile, shape and surface thereof during the manufacturing of the strand 10, together with measuring and detecting the specific anomalies/defect/faults along strand 10, which might be generated during the stranding process.

Thus, strand scanner 12 controls the quality of the manufacturing process of non-circular strand 10.

Strand scanner 12 is capable of examining strands 10 being produced as helical structures for wire ropes, cables and ropes applied for hoisting, mooring lines, communication lines, hauling, lifting, pulling, drilling, electrical conducting, tension member. Strands 10 are produced for having various non-circular shapes, configured to be linear and twisted, and constructed of rigid materials.

Strand scanner 12 examines the external surface of strand 10, and thus is capable of also examining strands 10 having various shapes, not limited to the above-mentioned description.

Non-circular twisted strand 10 is continuously shifted into, therethrough, and out of scanner 12, for being scanned thereby. During the scanning, strand 10 is examined regarding the twist extent, the distribution and the structure of strand 10, including the width versus the length thereof, for identifying anomalies from the pre-determined design to be manufactured by the stranding machine, and for identifying defects.

The term "shaft encoder" refers herein to an electro-mechanical device that converts the angular position or motion of a shaft or axle to an analog or digital code.

Strand scanner 12 counts the number of twists per length unit of strand 10, by a shaft encoder 20 counting the number of rotations of a disk 32 in relation to the linear displacement of strand 10, measured by a shaft encoder 16 counting the number of rotations of a linear motion pulley 14. Shaft encoders 16 and 20 may be replaced by other encoders.

In order to enable shaft encoder 20 be disposed away from the center of disk 32 and away from strand 10, disk 32 may rotate another wheel 18, via a gear system 46. Wheel 18 is disposed at the margin of disk 32, and wheel 18 is connected to rotation measurement shaft encoder 20. The rotation measurement shaft encoder 20 provides an electrical signal 20A corresponding to the rotation of wheel 18 thereof, and thus to that of disk 32.

A controller/computer 24 receives signal 20A from the rotation measurement shaft encoder 20.

The linear displacement of strand 10 is measured by linear motion pulley 14, having a known perimeter, thus each rotation thereof indicates the length of the perimeter. Linear motion pulley 14 may activate a wheel (not shown) of a linear displacement shaft encoder 16. Linear displacement shaft encoder 16 provides an electrical signal 16A corresponding to the rotation of linear motion pulley 14. Controller/computer 24 receives a signal 16A from linear displacement shaft encoder 16.

Linear motion pulley 14 functions as a linear displacement measurement system to measure the dynamical linear displacement of strand 10. The linear displacement measurement system includes linear motion pulley 14 driven by strand 10; and linear displacement shaft encoder 16, counting the rotations of linear motion pulley 14. The linear displacement of strand 10 can be measured in real time.

Controller/computer 24 receives signal 20A from rotation measurement shaft encoder 20, and signal 16A from linear displacement shaft encoder 16, and analyzes the two signals concurrently.

Preferably, the analysis is performed at pre-determined linear segments, being locations on strand 10, and/or at pre-determined angular segments, each segment being an examined sample, ranges thereof determined by controller 24.

For example, the linear displacement of strand 10 can be measured in specific pre-determined segments of the designed length of a cycle of twist, e.g., 42 centimeters, or a fraction thereof, e.g., 120 degrees.

Controller/computer 24 typically provides an angular differential to a linear differential, the differentials in relation to the angle and the location of the last sample. According to the above example, the expected result may be 120 degrees per 14 centimeters.

Figure 2:
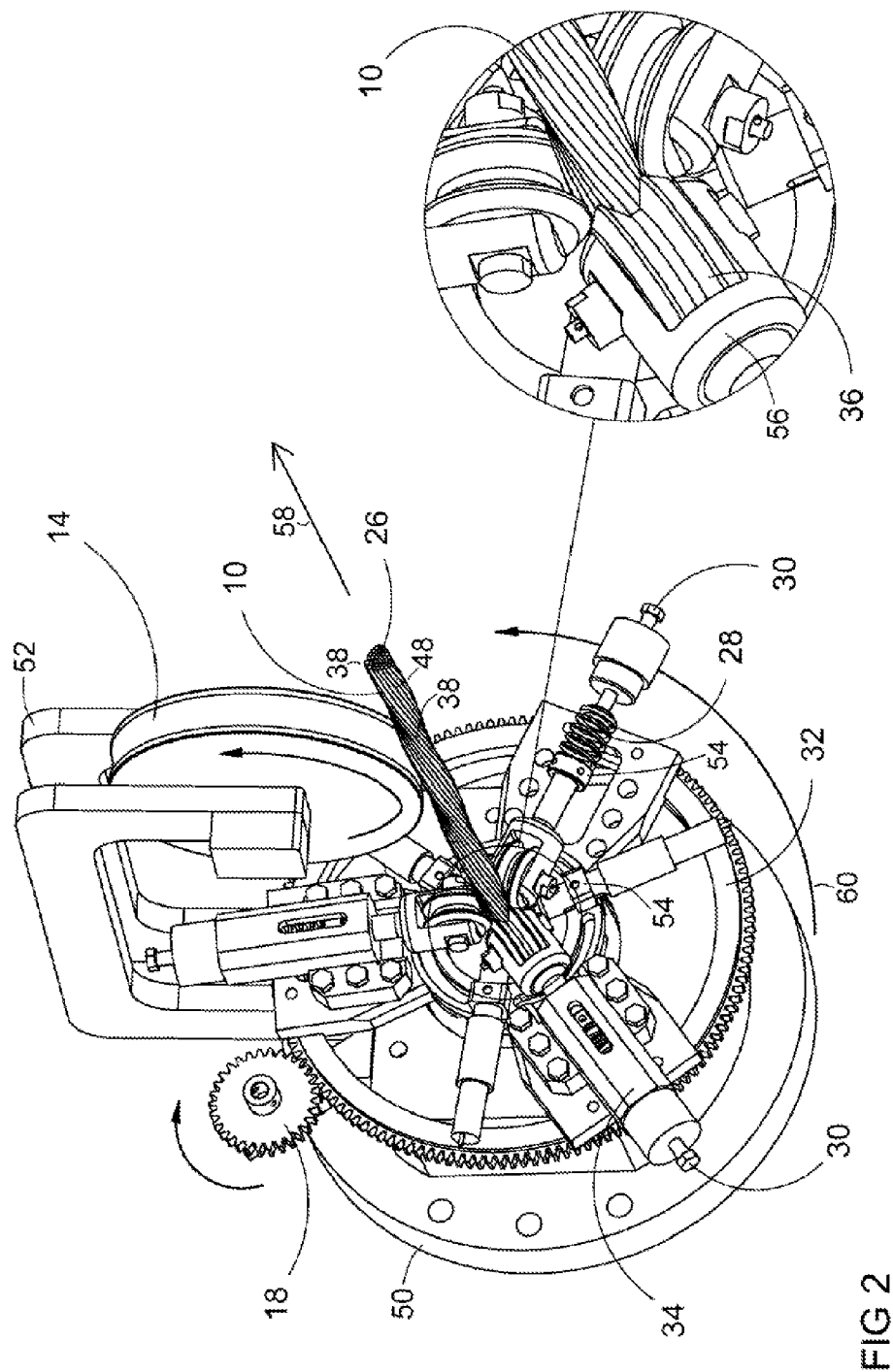
FIG. 2 is an enlarged view of the strand scanner of FIG. 1.

FIG. 2 is an enlarged view of the strand scanner of FIG. 1.

FIG. 2 depicts three embracing elements 36 disposed around strand 10, for embracing thereof. This embodiment of three embracing elements 36 is suited for a strand 10 having a triangular cross-section, depicted in the figures. The triangular cross-section includes a core 26 having a triangular cross-section, and wires 22 (not shown) braided around core 26.

Figure 3:
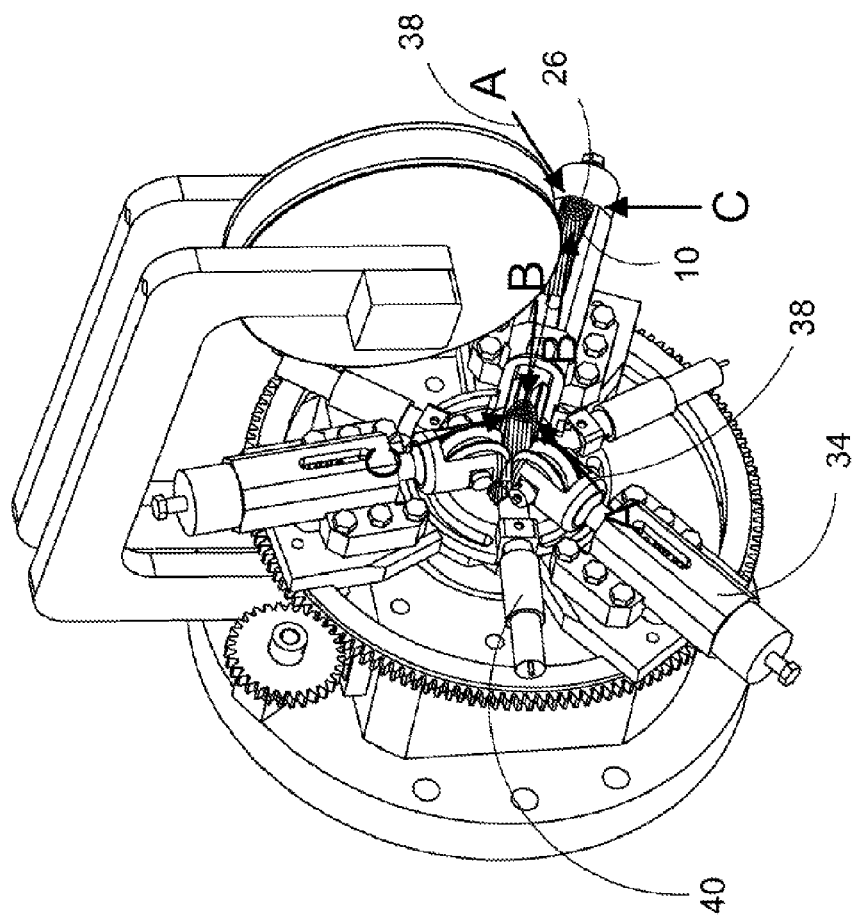
FIG. 3 shows the strand scanner of FIG. 1 having a cut in the strand, in order to demonstrate the strand twist and the rotation operated thereby.

The triangular cross-section comprises three vertexes 38, namely A, B, and C indicated in FIG. 3, and each embracing element 36 embraces one vertex 38.

Since strand 10 is twisted, meaning that the angular position of the vertexes 38 changes therealong, as indicated in two locations in the figure, the linear motion of strand 10 is converted into a rotational motion of embracing elements 36 sliding thereupon strand 10. Each embracing element 36 slides attached to the vertex 38 thereof upon strand 10.

According to another embodiment (not shown), each embracing element 36 embraces the flat surface 48 of strand 10.

A spring 28 and an adjusting screw 30 for adjusting the pressure of spring 28, may press embracing element 36 onto vertex 38 thereof in relation to the cylinder 34, or may allow to release the pressure therefrom, for getting free from one vertex, and for embracing another vertex 38. This replacement of the vertex may be necessary for cases of defects in strand 10. The pressure may be adjusted by adjusting screw 30 or by other means.

A four embracing elements 36 construction (not shown) surrounding strand 10, is suited for embracing a strand 10 having a quadrangular cross-section (not shown), for being rotated thereby.

The number of embracing elements 36 surrounding strand 10, the internal shape of embracing elements 36, and the pressure of springs 28, preferably are fitted to the expected vertex 38 or of the surface 48 of strand 10, for efficiently embracing strand 10, for being freely rotated thereby. In particular, embracing elements 36 preferably are shaped to be complementary to the shape of vertexes 38.

Embracing elements 36 function as shoes, and may constitute pulleys or skates being free to rotate for sliding along the linear direction of strand 10, thus substantially being floating.

The embracing of strand 10 by embracing elements 36 is obtained by the non-circular character of strand 10, and not by friction force, such as by tight gripping. Vertexes 38, even if not sharp, such as in an ellipse, constitute the non-circular character of strand 10. Thus, the embracing of strand 10 by embracing elements 36 allows sliding embracing elements 36 along strand 10.

Embracing elements (36) substantially evenly surround strand 10, thus they do not bend the strand.

The twisted shape surface of the strand 10 rotates the three embracing elements 36 in direction 60 being perpendicular to the longitudinal position 58 of strand 10.

The cylinders 34 of embracing elements 36 are rigidly fixed to disk 32. A piston 54 is movable within each cylinder 34. Spring 28 presses piston 54 towards strand 10. A fork 56 is rigidly fixed to piston 54. Embracing element 36 is pivotally connected to fork 56. Thus, rotation of embracing elements 36 perpendicular to strand 10 rotates disk 32.

Disk 32 rotates wheel 18, being connected to rotation measurement shaft encoder 20 and from there to controller 24.

Linear motion pulley 14 is rotated by strand 10 due to friction therebetween, thus rotating the wheel (not shown) of linear displacement shaft encoder 16. Linear displacement shaft encoder 16 is connected to controller 24, thus measuring the linear displacement of the strand 10.

Thus, strand scanner 12 includes a dynamical mechanism including embracing elements 36 following and measuring the lay length of the non-circular twisted strand 10 and of the surface quality of the strand.

The dynamical mechanism includes embracing elements 36 being radially disposed around the strand axis. Embracing elements 36 are preferably fitted to the profile of the expected strand 10. For example: for triangular strand, there should be three individual embracing elements 36. For oval or flat strands, there should be two individual embracing elements 36.

Embracing elements 36 are radially pressed by spring 28 or by any compression mechanisms which may ensure the optimal contact between embracing elements 36 and strand 10. Accordingly, the linear movement of the twisted strand 10 is converted to a rotational movement of embracing elements 36 and thus of the disk 32.

Embracing elements 36 are made of steel or any rigid material. The material of the pulleys may fit the material of strand 10, for avoiding damage to the strand surface, due to the radial compression.

Disk 32, being rigidly fixed to cylinders 34, is rotated by embracing elements 36, being rotated by strand 10, in relation to a stationary base 50 via radial bearings (not shown).

Linear motion pulley 14 is rotated by strand 10, in relation to a rack and fork 52, being fixed to base 50. Rack and fork 52, being fixed to base 50, provide that linear motion pulley 14 fixed thereto, substantially does not measure the length of the twist along strand 10.

According to another embodiment, the linear motion of strand 10 may be measured by counting rotations of embracing elements 36. This embodiment is not preferable since it measures the length of the twist along strand 10.

Base 50 may be fixed to the stranding machine (not shown) at the outlet stage/station thereof, i.e. close to the collecting spool of strand 10, or may be disposed at a further location.

FIG. 3 shows the strand scanner of FIG. 1 having an imaginary cut in the strand, in order to demonstrate the strand twist and the rotation operated thereby.

At the linear location where strand 10 exits the strand scanner 12, vertexes 38 of strand 10 are marked in the figure at two different linear locations thereof, with letters A, B, and C. Due to the twisted shape of the strand 10 the position of the letters is rotated from one location to another. For example, the letter A at one location of the strand is rotated from the letter A at the other locations thereof.

Cylinder 34 functions as a track for the spring 28 pressing embracing elements 36.

Strand scanner 12 may further include surface sensors 40 for measuring the texture of the "flat" surface 48 (shown in FIG. 4) of strand 10. For example, surface sensor 40 may indicate the presence of a protrusion at a certain area on flat surface 48, being a defect. Any of surface sensors 40 may detect the defect and may stop the entire machine from processing the manufacturing of strand 10.

Figure 4:
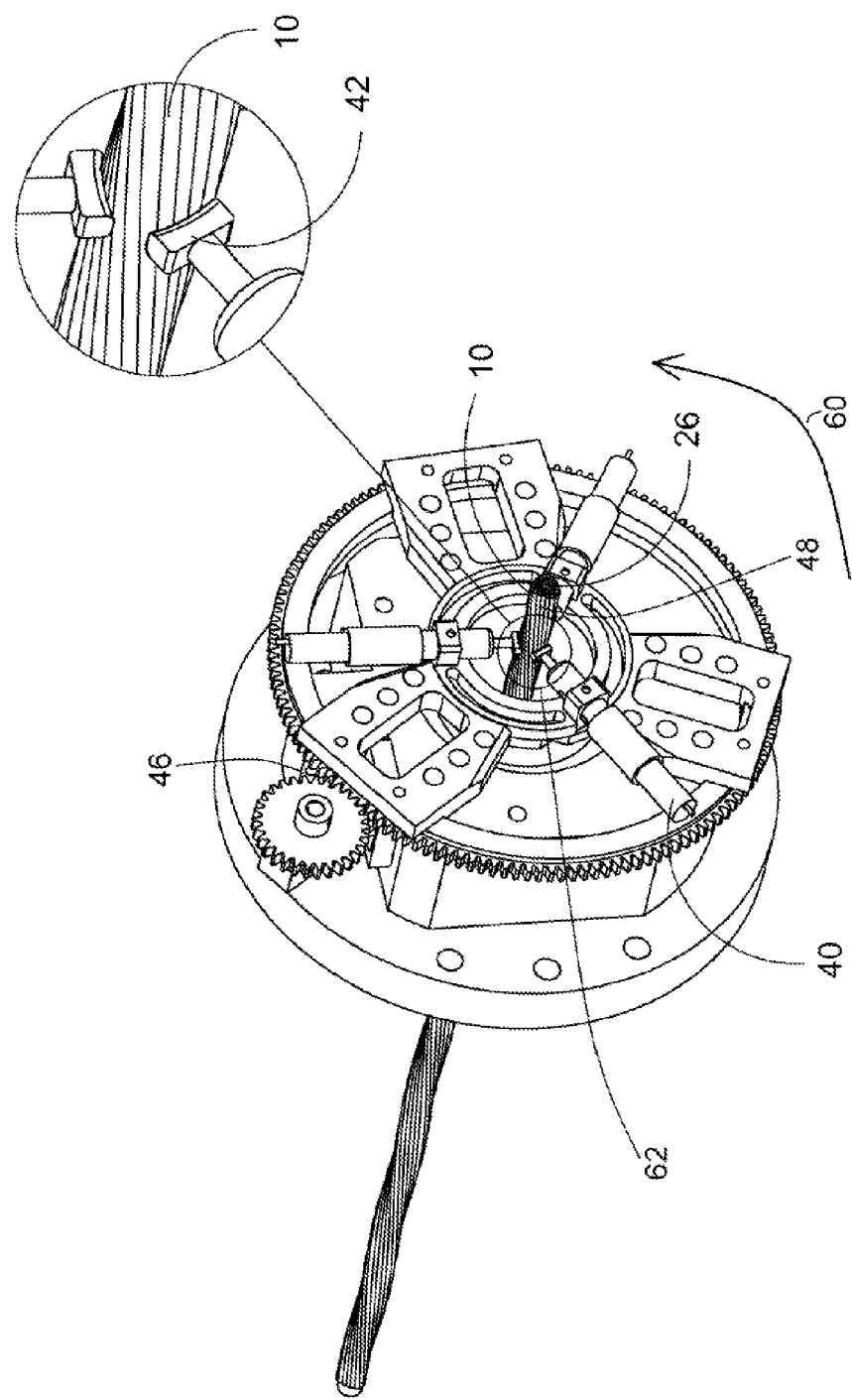
FIG. 4 shows a perspective view and an enlargement of the strand surface sensors 40 of FIG. 3.

FIG. 4 shows a perspective view and an enlargement of the strand surface sensors 40 of FIG. 3.

Each of surface sensors 40 ends with an end surface 42. End surface 42 slides upon and along one of flat surfaces 48 of strand surface 10.

End surface 42 of surface sensor 40 rotates together with the disk 32 and embracing elements 36, and thus the flat surface 48 of strand 10 is expected to be unchangeable during the scanning in spite of all the movements. Thus, any change is reported to be a defect in the surface of the strand 10.

The term "brush element" refers herein to a circular device for conducting electric current between stationary wires and moving parts, most commonly in a rotating shaft.

Unlike rotation measurement shaft encoder 20 and linear displacement shaft encoder 16, recording the direct rotation count of disk 32 and of linear motion pulley 14 respectively, the axle thereof being stationary, end surfaces 42 of surface sensors 40 are not stationary, since they rotate together with the disk 32 and with embracing elements 36. Thus, a brush element 62 conducts the electric signals produced by surface sensors 40 to a stationary location, such as to controller 24 (not shown).

Surface sensors 40 measure the surface roughness and principal dimensions of the twisted strand 10. The measurement approves triangular attitude in the case of triangular strands, principal diameters in the case of oval and flat strands and any principal dimensions in non-circular strands 10.

Surface sensors 40 are disposed near embracing elements 36 and can be radially positioned to maintain an optimal contact with the strand circular shape.

The term "LVDT" refers herein to a Linear Variable Differential Transformer, being an electrical transformer used for measuring linear displacement.

Surface sensors 40 may be of any position measurements sensors, such as: LVDT, proximity magnetic, optical etc.

Surface sensors 40 may rotate with disk 32 while following on the quality of the strand surface 48, thus detecting anomaly thereon, such as upstanding wire, change in strand diameter, etc.

Gear system 46 transmits the rotational displacement of disk 32 to a rotational motion of wheel 18. Gear system 46 may constitute a belt gear system or a teeth gear system.

A data acquisition system, which may be included in controller 24, records the actual rotational position of the disk 32 and the strand linear displacement. The data acquisition system can be any PLC (Programmable Logic Controller) instrument or any computerized system with the appropriate software and A/D (Analog to Digital) or D/A systems.

A computerized software application, programmed according to the expected characteristics of strand 10, as produced by the stranding machine (not shown), and a specific measurement application, simultaneously calculate the local lay length/twist level of the strand by dividing the recorded data of the linear displacement of strand 10 by the rotational displacement of disk 32. This can be conducted into individual segments. The size and level of segments is defined by the operator.

For each segment, the program may divide the local measured rotational displacement of disk 32 by the local linear displacement of the strand 10. Accordingly, the local twist/lay length is measured and calculated. The computerized software application calculates the main actual dimensions of the strand 10 as measured by the radial position sensors.

A visual display (not shown) displays the local lay length of strand 10. This visual display may plot the lay length/twist level of the strand versus the strand linear location. The visual display may include the upper and lower limits of the required twist level.

An alarm element may execute a vocal alert generator or a red light activator. This alarm may be activated when the level of twist deviates from the required range. The alarm may be activated when any deviation is detected by the radial sensors.

A shut down system may include an electrical connection to the electrical board of the stranding machine. When the alarm is activated due to over twist/low twist, anomaly at the surface, or fault in a principal strand dimension, the shutdown system may generate shut down of the stranding machine.

The strand scanner 12 preferably is automatically operated during the stranding process. It is positioned proximate to the strand spool at the front of the stranding machine.

The strand scanner 12 preferably is designed for heavy duty stranding operations, such as up to 5,000 meters continuous measurement. It is preferably designed for strand sizes, such as for a range of 5-25 mm triangular attitude, and of similar diameter for oval strands. The strand scanner 12 preferably requires simple and fast preparation for process. The local twist level of the strand may be measured at relatively very small segments, such as every 50 mm.

In the figures and/or description herein, the following reference numerals (Reference Signs List) have been mentioned:

numeral 10 denotes a strand to be examined;
numeral 12 denotes a system for scanning a strand, according to one embodiment of the present invention;
numeral 14 denotes a linear motion pulley, being a pulley for measuring linear motion of the strand;
numeral 16 denotes a shaft encoder, for measuring the linear displacement of the strand;
numeral 16A denotes a signal;
numeral 18 denotes a wheel;
numeral 20 denotes a shaft encoder, for measuring the rotation of the disk;
numeral 20A denotes a signal;
numeral 22 denotes a wire wrapped around the core of the strand;
numeral 24 denotes a controller;
numeral 26 denotes the core of the strand;
numeral 28 denotes a spring, for pressing the embracing element on the strand;

numeral 30 denotes a screw, for adjusting the pressure of the spring;
numeral 32 denotes a disk;
numeral 34 denotes a cylinder, for housing the spring;
numeral 36 denotes an embracing element, for embracing the strand, while sliding along the strand;
numeral 38 denotes a vertex of the strand;
numeral 40 denotes a surface sensor, for sensing a surface quality of the strand;
numeral 42 denotes an end surface of the surface sensor;
numeral 46 denotes a gear system;
numeral 48 denotes a flat surface of the strand;
numeral 50 denotes a base, being the stationary element, in relation to which the measurements are conducted;
numeral 52 denotes a rack and fork, being fixed to the base, and being rotatably connected to the linear motion pulley;
numeral 54 denotes a piston, for carrying the fork of the pulley;
numeral 56 denotes the fork of the pulley;
numeral 58 denotes the longitudinal position of the strand;
numeral 60 denotes the direction of motion of the disk;
numeral 62 denotes a brush element.

The foregoing description and illustrations of the embodiments of the invention has been presented for the purposes of illustration. It is not intended to be exhaustive or to limit the invention to the above description in any form.

Any term that has been defined above and used in the claims, should to be interpreted according to this definition.

The reference numbers in the claims are not a part of the claims, but rather used for facilitating the reading thereof. These reference numbers should not be interpreted as limiting the claims in any form.

The invention claimed is:

1. A system (12) for measuring geometry of a non-circular twisted strand (10) during a stranding process, said system comprising:
   a pulley (14), for being rotated by linear displacement of the strand (10) induced by said stranding process;
   a first encoder (16), for measuring the rotation of said pulley (14) in relation to a stationary base (50), thereby measuring said linear displacement of the strand (10);
   at least one embracing element (36), for embracing a vertex (38) or another zone (48) of said strand (10), for being rotated perpendicular (60) to the longitudinal position (58) of the strand (10) upon said linear displacement thereof, due to the twist thereof, said embracing obtained by the non-circular character of the strand (10) rather than by friction, thereby allowing sliding said at least one embracing element (36) therealong; and
   a second encoder (20), for measuring said rotation of said at least one embracing element (36) perpendicular (60) to the longitudinal position (58) of the strand (10) in relation to said stationary base (50),
   thereby concurrent measurement of said linear displacement of the strand (10) and of said rotation of said at least one embracing element (36) provides a measurement of the twist character of the strand (10).

2. A system (12) according to claim 1, wherein the number of said at least one embracing element (36) comprises the number of vertexes (38) of said strand (10) designed to be produced by said stranding process,
   thereby each of the embracing elements (36) embraces one of said vertexes (38).

3. A system (12) according to claim 1, wherein said at least one embracing element (36) is shaped substantially complementary to a shape of the vertexes (38) of said strand (10) designed to be produced by said stranding process.

4. A system (12) according to claim 1, wherein said at least one embracing element (36) comprises at least one pulley, for freely rotating along and upon the strand (10).

5. A system (12) according to claim 1, wherein said at least one embracing element (36) comprises a springy element (28), for pressing said at least one embracing element (36) on the strand (10).

6. A system (12) according to claim 1, wherein said at least one embracing element (36) comprises a plurality of embracing elements (36) surrounding the strand (10),
   thereby avoiding bending the strand (10).

7. A system (12) according to claim 1, further comprising:
   at least one slideable surface sensor (40), for traveling together with said at least one embracing element (36), and for sliding along and attached to a zone (48) of the strand (10), for detecting deviations of a surface of said zone (48) from a pre-determined design of said stranding process.

8. A system (12) according to claim 7, wherein said at least one slideable surface sensor (40) comprises a position measurement sensor, for detecting said deviations.

9. A system (12) according to claim 7, wherein said at least one slideable surface sensor (40) comprises a brush element (62) for conducting electric signals from said at least one slideable surface sensor (40) to a stationary location (24).

10. A system (12) according to claim 1, further comprising:
    a disk (32), connected to said at least one embracing element (36), for being rotated thereby perpendicular (60) to the longitudinal position (58) of the strand (10).

11. A system (12) according to claim 10, further comprising:
    at least one springy element (28), for pressing said at least one embracing element (36) from said disk (32) onto the strand (10).

12. A system (12) according to claim 10, further comprising:
    a wheel (18) disposed at a margin of said disk (32), for being rotated by said disk (32) via a gear system (46), wherein said wheel (18) is connected to said second encoder (20),
    thereby said second encoder (20) is disposed away from a center of said disk (32).

13. A system (12) according to claim 1, further comprising:
    a controller (24), for determining samples for said measurements,
    thereby said measurements do not accumulate errors.

14. A system (12) according to claim 13, wherein said samples comprise members selected from a group including: length segments, angular segments.

15. A method for measuring geometry of a non-circular twisted strand (10) during a stranding process, said method comprising the steps of:
    rotating a pulley (14) by linear displacement of the strand (10) induced by said stranding process;
    measuring, by a first encoder (16), the rotation of said pulley (14), thereby measuring said linear displacement of the strand (10);
    embracing, by at least one embracing element (36), a vertex (38) or another zone (48) of said strand (10), for rotating said at least one embracing element (36) perpendicular (60) to the longitudinal position (58) of the strand (10) upon said linear displacement thereof, due to the twist thereof; and measuring, by a second encoder (20), said rotation of said at least one embracing element (36) perpendicular (60) to the longitudinal position (58) of the strand (10), thereby concurrent measurement of said linear displacement of the strand (10) and of said rotation of said at least one embracing element (36), provides a measurement of the twist character of the strand (10).

16. A method according to claim 15, wherein said embracing of the vertex (38) or another zone (48) of said strand (10) comprises free linear displacement of the strand (10) in relation to said at least one embracing element (36).

17. A method according to claim 15, further comprising the steps of:

rotating at least one slideable surface sensor (40) together with said at least two embracing element (36); and detecting by said at least one slideable surface sensor (40) deviations of a surface of said strand (10) from a predetermined design of said stranding process.

18. A method according to claim 15, further comprising the steps of:

upon exceeding a pre-determined threshold of measurement, halting the standing process.

19. A method according to claim 15, wherein said measurements are conducted upon pre-determined samples of the strand (10), thereby said measurements do not accumulate errors.

20. A method according to claim 19, wherein said pre-determined samples comprise members selected from a group including: length segments, angular segments.

\* \* \* \* \*